United States Patent [19]

Nichols

[11] 4,321,923
[45] Mar. 30, 1982

[54] LOW PROFILE SHUT-OFF VALVE FOR MEDICAL SUCTION APPARATUS

[76] Inventor: Robert L. Nichols, 808 Fort Worth St., Jacksonville, Tex. 75766

[21] Appl. No.: 117,058

[22] Filed: Jan. 31, 1980

[51] Int. Cl.³ .............................................. A61M 1/00
[52] U.S. Cl. .................................... 128/276; 137/205
[58] Field of Search ............... 128/276, 277, 278, 760, 128/766; 137/205, 202, 433; 15/353

[56] References Cited

U.S. PATENT DOCUMENTS

| | | | |
|---|---|---|---|
| 3,290,865 | 12/1966 | Serou et al. | 15/353 |
| 3,685,517 | 8/1972 | Reynolds et al. | 128/277 |
| 3,719,197 | 3/1973 | Pannier et al. | 137/205 |
| 3,780,738 | 12/1973 | Deaton | 128/277 |
| 3,805,788 | 4/1974 | Kleiner | 128/276 |
| 3,811,485 | 5/1974 | Holbrook | 141/59 |
| 3,827,452 | 8/1974 | Baumgarten | 137/205 |
| 3,960,165 | 6/1976 | Holbrook et al. | 137/202 |
| 3,965,902 | 6/1976 | Reilly et al. | 128/276 |
| 3,965,903 | 6/1976 | Cranager | 128/276 |
| 3,989,046 | 11/1976 | Pannier et al. | 128/276 |
| 3,993,067 | 11/1976 | Schachet et al. | 128/214 |
| 4,013,076 | 3/1977 | Puderbaugh | 128/276 |
| 4,111,204 | 9/1978 | Hessel | 128/276 |
| 4,228,798 | 10/1980 | Deaton | 128/276 |
| 4,245,637 | 1/1981 | Nichols | 128/276 |

FOREIGN PATENT DOCUMENTS

| | | | |
|---|---|---|---|
| 665265 | 6/1963 | Canada | 15/470 |
| 660696 | 11/1951 | United Kingdom | 137/205 |

Primary Examiner—Robert W. Michell
Assistant Examiner—J. L. Kruter
Attorney, Agent, or Firm—Richards, Harris & Medlock

[57] ABSTRACT

A low profile basket and float assembly shut-off valve for the vacuum port in medical suction apparatus is disclosed. An open-topped cup-like basket depends downwardly from a container cover below the vacuum port and has one or more upper vacuum communication passages and one or more lower fluid communication openings. The basket has a closed-top central sleeve extending integrally upwardly from the bottom thereof. A complementally configured float is disposed within the basket and is a sombrero-like-shaped member having a central upstanding crown with a peripheral brim extending laterally from the base of the crown and turned upwardly. The central crown forms a reception sleeve sliding along the basket sleeve in telescoping relation. The peripheral brim provides a floatation surface. A gap is provided between the bottoms of the float and basket in a downward open-valve position of the float to prevent liquid surface-tension impedance to upward movement of the float. The float carries a flexible disc at the top of the crown. The disc is concave towards the vacuum port. There is permitted a limited amount of post-travel of the float upwardly beyond initial engagement between the disc and the vacuum port. An annular auxiliary sealing support is provided on top of the crown below and incentric to the outer periphery of the disc.

21 Claims, 3 Drawing Figures

LOW PROFILE SHUT-OFF VALVE FOR MEDICAL SUCTION APPARATUS

TECHNICAL FIELD

The present invention relates to medical suction apparatus including a fluid container with a cover having a patient port for receiving fluid from the body of a patient and a vacuum port for establishing a vacuum in the container for drawing fluid through the patient port, and more particularly to a shut-off valve for the vacuum port.

BACKGROUND ART

Medical suction apparatus has long been used in hospitals to remove fluid from a patient during various medical procedures. One type of apparatus commonly used to receive and contain fluid from a patient includes a canister or container covered by a cover, with a patient port and a vacuum port communicating through the cover. A tubular vacuum line is attached between a vacuum source and the vacuum port, and another tubular line is connected to the patient port for withdrawing fluid from the patient, through the patient port and into the container. A shut-off valve is normally used to close or block the vacuum port when the fluid within the container rises to a predetermined level. This prevents the patient fluid from entering and damaging or contaminating the hospital vacuum system.

In order to maximize use of hospital shelf space, it is desirable to store the cover and container in a pre-assembled condition. The containers are commonly frustoconical cup-like members amenable to efficient stacking with a minimum of vertical dead space therebetween. The covers, however, typically have the shut-off valve assembly depending downwardly from the underside thereof by a substantial vertical dimension below the vacuum port which significantly impairs efficient stacking of the covers.

A need has thus arisen for a low profile shut-off valve assembly with minimum vertical extension, and which yet provides excellent vacuum shut-off capabilities.

SUMMARY OF THE INVENTION

The present invention provides a low profile shut-off valve assembly and further provides significant improvements in valve-closing action.

In medical suction apparatus having a container and cover with a patient port and vacuum port, the invention provides a basket and float assembly shut-off valve for the vacuum port. The basket depends downwardly from the cover below the vacuum port and has one or more upper vacuum communication passages and one or more lower fluid communication openings. The float is disposed within the basket and has a peripheral floatation surface. The basket and float have complementally interfitting guiding structure incentric to the peripheral floatation surface of the float for guiding the float upwardly to close the vacuum port in response to rising fluid level in the container entering the basket through the one or more lower openings. The floatation surface of the float is uniformly concentric about the guiding structure to provide substantially flush floatation and to provide in combination with the maximized surface area afforded thereby an enhanced valve-closing force.

In another aspect of the invention, a limited amount of post-travel of the float upwardly beyond initial seal engagement with the vacuum port is provided to improve vertical dimensional deviation tolerance. This enables a shorter vertical stroke without increased manufacturing costs.

In another aspect of the invention, an annular auxiliary sealing support is provided for enhanced sealing during post-travel of the float. This auxiliary sealing support further provides a back-up seal in the case of extended over-travel.

In another aspect of the invention, upward movement of the float is enhanced by preventing liquid surface-tension impedance between the float and basket.

In another aspect of the invention, simple and efficient structure is provided affording the aforenoted and other advantages. The basket and float assembly may be stored separately and quickly atached to the cover at the time of use. Alternatively, the cover may be stored with the basket and float assembly mounted thereto. In addition to simplicity, the invention enables a minimum number of components to accomplish improved results. The invention thus affords both lower costs and better performance over prior shut-off valve assemblies.

DETAILED DESCRIPTION

Figure 1:
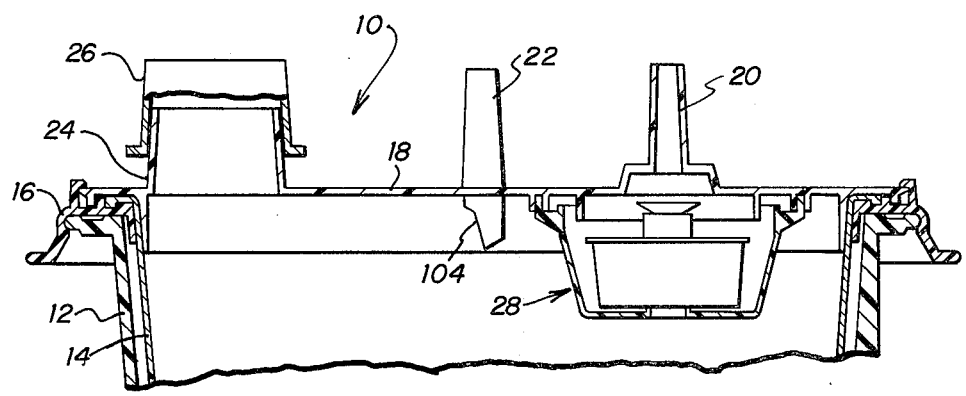
FIG. 1 is a partial cross sectional view of medical suction apparatus constructed in accordance with the invention, including a container, cover, and basket and float assembly.

There is shown in FIG. 1 medical suction apparatus 10 constructed in accordance with the invention. The apparatus includes a generally cylindrical open-topped container 12, which may be slightly frustoconical for pre-use stacking. The container may include a semi-rigid plastic disposable liner 14 with an annular peripheral lid 16 supported on the container rim. The container is closed by a cover 18 coacting with container liner lid 16 in push down snap-in relation. This type of container and mounting arrangement is disclosed and claimed in the co-pending patent application entitled "Medical Receptacle With Disposable Liner Assembly", Ser. No. 113,620 filed Jan. 21, 1980. Various types of other containers and mounting arrangements may be used with the present shut-off valve.

The cover 18 has a vacuum port 20 connectable to a suitable vacuum source for establishing a vacuum within the container. The cover has a patient port 22 for drawing fluid from the body of a patient through a tubular connection for collection within the container. The cover may also include a pour spout 24 and removable cap 26.

Figure 2:
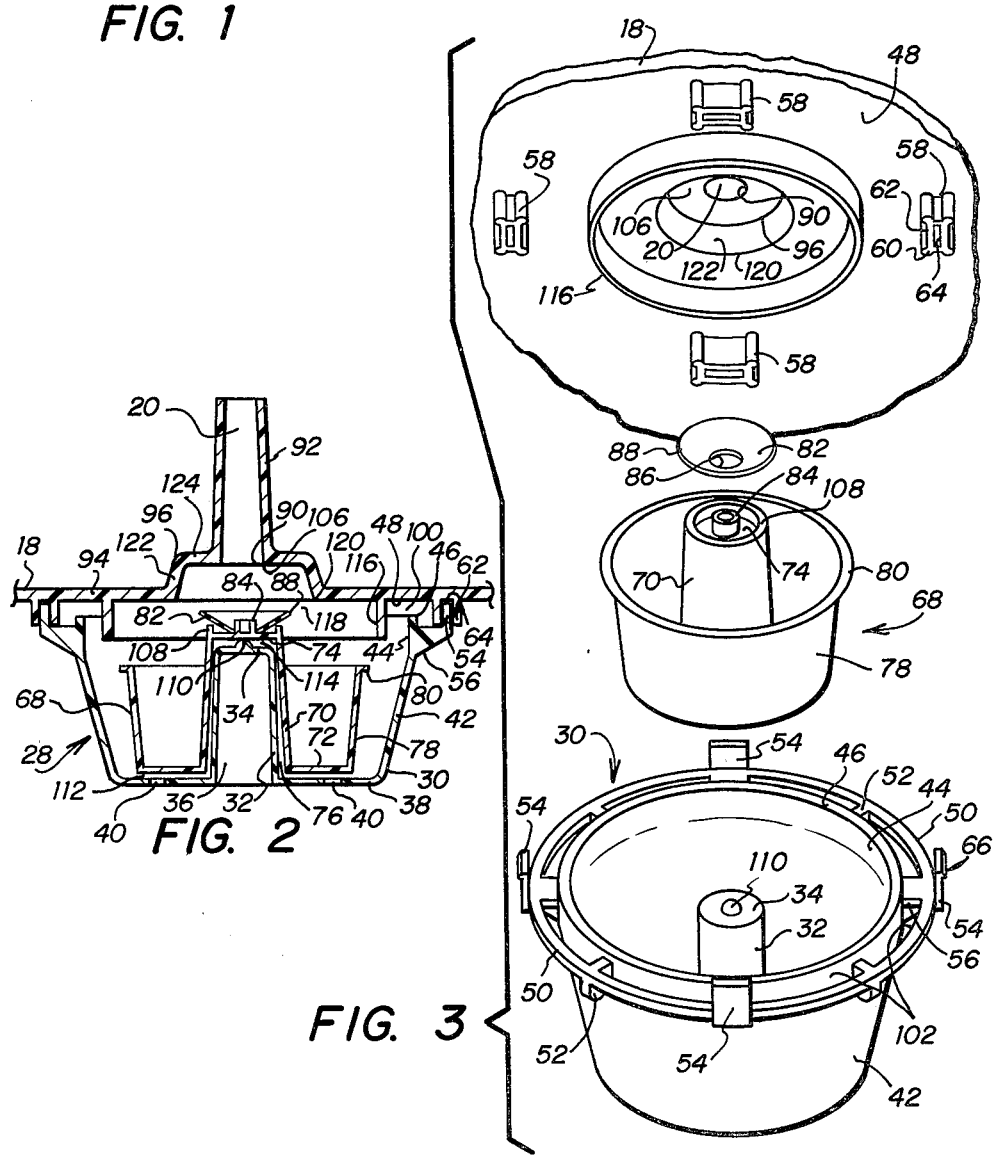
FIG. 2 is a cross sectional view of the basket and float assembly and a portion of the cover of FIG. 1.
Figure 3:
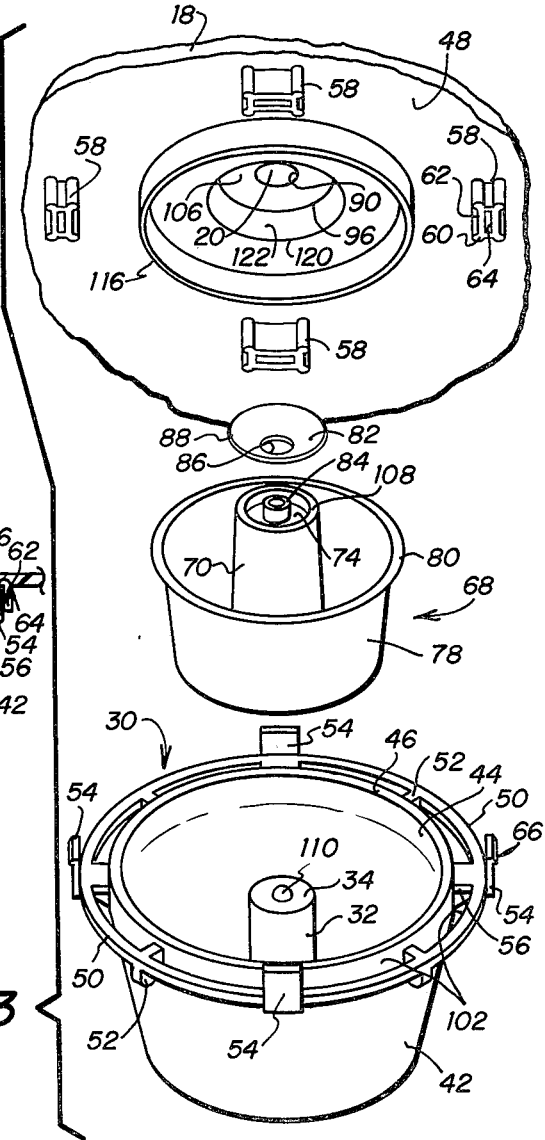
FIG. 3 is an exploded isometric view of the basket and float assembly and cover of FIG. 2.

Depending downwardly from the cover below vacuum port 20 is a low profile basket and float assembly shut-off valve 28. Referring to FIGS. 2 and 3, basket 30 is an open-topped cup-like member having a central vertical tubular sleeve 32 integrally extending upwardly from the bottom thereof. This basket sleeve 32 has annular sidewalls tapered slightly inwardly as they extend upwardly and hence the sleeve is slightly frustoconical. The sleeve has a closed top 34 to thus form a centrally raised downwardly opening elongated cavity 36. The annular horizontal bottom 38 of the basket has one or more openings or apertures 40 formed therethrough for fluid communication. The outer annular wall 42 of the basket diverges slightly outwardly as it extends upwardly. This outer wall 42 has an upper section 44 which is substantially vertical and terminates at an upper lip 46 spaced below the underside 48 of cover 18.

Upper outer wall section 44 has a lateral peripheral annular rim 50, FIG. 3, spaced therefrom and integrally supported thereon by a plurality of radial peripherally spaced support spokes 52. Integrally formed on the outer periphery of rim 50 and extending upwardly therefrom are a plurality of mounting tabs 54 further supported by additional bolster spokes 56. Integrally formed on the underside 48 of cover 18 and extending downwardly therefrom are a plurality of reception pockets 58 peripherally spaced and concentric to vacuum port 20. Each pocket has four corner edge supports 60 extending vertically downwardly with walls 62 extending therebetween defining a rectangular slot 64. Mounting tabs 54 are inserted into slots 64 providing a tight frictionally retained fit. This provides accurate alignment of basket and float assembly 28 with the vacuum port 20. Mounting tabs 54 may be provided with pointed gripping fingers 66 for enhanced retention.

Disposed within basket 30 and complementally configured thereto is float 68. The float is an open-topped cup-like member having a generally tubular vertical reception sleeve 70 integrally extending upwardly from the bottom 72 of the float. Float sleeve 70 has an annular side wall slightly tapered inwardly as it extends upwardly to be slightly frustoconical. The sleeve has a closed top 74 to thus form a centrally raised elongated downwardly opening cavity 76. Basket sleeve 32 forms a vertical guide stalk and substantially fills the lateral dimension of float cavity 76. Basket sleeve 32 substantially fills the vertical dimension of float cavity 76 when the float is in a downward open-valve position as shown in FIG. 2.

The bottom surface 72 of the float extends laterally from the base of reception sleeve 70 and forms an annular peripheral horizontal floatation surface uniformly concentric to sleeve 70. The float has an outer annular sidewall 78 extending upwardly and slightly outwardly. Sidewall 78 terminates at upper outwardly turned peripheral lip 80 whose upper reach does not extend as high as top wall 74. Float 68 thus comprises a sombrero-like-shaped member having a central upstanding crown formed by top 74 and reception sleeve 70. The sombrero-like-shaped float has a peripheral brim extending laterally from the base of the crown and then turned upwardly. The brim is formed by bottom surface 72 and outer sidewall 78.

Mounted on the top side of top surface 74 of the float is a resilient rubber disc 82. Top surface 74 has an integral support post 84 extending upwardly. The disc has a central aperture 86 through which post 84 extends in sealing relation. The disc is concave towards vacuum port 20 and has an outer peripheral lip 88 defining a lateral diameter greater than the diameter of the mouth 90 of the vacuum port. The vacuum port mouth 90 has a frustoconical neck 92 extending upwardly therefrom. Mouth 90 is displaced above the main plane 94 of cover 18 by a raised annular shoulder 96 having a larger diameter than mouth 90. The diameter of shoulder 96 is also larger than the diameter defined by peripheral disc lip 88.

In operation, vacuum is communicated via port 20 through the annular gap passage 100 between basket lip 46 and cover undersurface 48, and through arcuate passage apertures 102 in basket rim 50, to the interior of container 12. This vacuum within container 12 draws fluids from the body of a patient via a tubular connection to patient port 22. Port 22 has a lower spout 104 for discharging the fluid within container 12. As the fluid level within the container rises, it reaches basket bottom 38 and thereafter enters the basket through lower fluid communication openings 40. Rising fluid level within basket 30 effects floatation of float 68. The float rises upwardly along basket sleeve 32. When a predetermined fluid level is reached, disc lip 88 engages the horizontal annular underside 106 around mouth 90 to sealingly close vacuum port 20. This shuts off the application of vacuum to the interior of the container and prevents fluid from being drawn into the hospital vacuum system.

The pair of tubular vertical integrally formed basket and float sleeves 32 and 70 thus provide a complementally interfitting guiding structure incentric to peripheral annular floatation surface 72. This guiding structure guides float 68 upwardly to close vacuum port 20 around mouth 90 in response to rising fluid level in container 12 entering basket 30 through the one or more lower fluid communication openings 40. The incentric guiding structure and the telescoping relation of the sleeves provides superior vertical guiding with minimum lateral free play. This provides both accurate alignment with vacuum port 20 and substantially flush upward movement of float 68.

The sliding interfitting reciprocal telescoping relation of the sleeves and the flush aligned float movement provided thereby significantly improves the sealing characteristics of the shut-off valve. Canting of the float during its upward movement is substantially eliminated. This ensures an annularly uniform tight seal between disc edge 88 and surface 106 of the vacuum port.

Flush upward floatation of float 68 is further enhanced by the annular, uniformly concentric flotation surface 72. Since surface 72 is concentric to the central guiding structure provided by sleeves 32 and 70, the floating surface area is maximized. This maximization of floatation surface area in combination with the uniform concentricity thereof further enhances flush, upward, buoyed movement of float 68. This maximization of floatation surface area further provides an enhanced valve-closing force whereby to provide an increased sealing force of disc 82 against surface 106. Even if there is some slight canting of the float due to the necessary clearances between the sleeves, this increased valve-closing sealing force will compensate such slight canting. The basket and float assembly in combination thus provide significant sealing characteristics.

Upon engagement of disc lip 88 with surface 106 of the vacuum port, the float may continue to rise a short distance. This limited amount of post-travel after seal engagement is significant because it enables a greater vertical dimensional deviation tolerance in the manufactured parts. This in turn enables a short vertical stroke affording a shallow low profile shut-off valve without resorting to expensive manufacturing techniques requiring extremely high degrees of dimensional precision. The limited amount of post-travel can tolerate a higher degree of deviation from specified dimensions, which can become significant on a percentage error basis in a short stroke.

The seal around mouth 90 of the vacuum port is further enhanced by a short upward annular extension 108 of float reception sleeve 70. Extension 108 extends above top wall 74 and forms an auxiliary annular sealing support. In the open-valve position of the float shown in FIG. 2, the underside of disc 82 rests against or is spaced slightly above auxiliary support 108. As the float moves upwardly and disc lip 88 engages surface 106, auxiliary sealing support 108 will bear against the undersurface of disc 82 with increasing pressure. The amount of post-travel of the float will be determined in part by the resiliency of disc 82. During this post-travel, sealing support 108 forms an auxiliary seal against disc 82, in addition to the seal around support post 84 through aperture 86, to thus provide a double seal against leakage along such path.

Annular sealing support 108 also enhances the sealing engagement between disc lip 88 and surface 106 because support 108 is closer to lip 88 than is support 84. This provides auxiliary support for peripheral lip 88 against unsealed deformation thereof.

Sealing support 108 further provides a back-up seal in the case of extended post-travel. If the float moves far enough upwardly, support 108 will pinch disc 82 against surface 106 and provide an annularly localized pressure sealing line around mouth 90.

The top 34 of sleeve 32 is provided with an integral upwardly protruded bump 110. This bump provides point contact means with the undersurface of the top 74 of float sleeve 70. In the downward open-valve position of the float as shown in FIG. 2, bump 110 provides stop means preventing further downward movement of float 68. Bump 110 establishes an annular gap 112 between float bottom 72 and basket bottom 38. Bump 110 further establishes a gap 114 between float top 74 and basket top 34.

Gaps 112 and 114 are significant for preventing liquid surface-tension impedance to upward movement of float 68. Fluid entering the basket through openings 40 will cling to surfaces therein as a film of given depth. If float bottom 72 rests on basket bottom 38, the entering fluid can creep along this interface by capillary action and produce a clinging force between these two surfaces. This clinging force resists upward movement of the float. Capillary fluid action upwardly along the interface between sleeves 32 and 70 may continue to the interface between float top 74 and basket top 34. This produces additional clinging surface-tension force at the interface between float top 74 and basket top 34, which further impedes upward movement of the float. The stop means provided by bump 110 coacts between sleeve 32 and sleeve 70 to provide gaps 112 and 114 so as to prevent coalescense of the liquid surface-tension films on the opposing faces of the gaps. The liquid surface-tension film along the vertical interface between sleeves 32 and 70 does not significantly impede upward movement of the float. This is because of the shearing force effected on any film along such vertical interface during upward float movement.

Cover 18 has a downwardly depending annular flange 116 concentric to vaccum port 20 and incentric to basket rim 46. This flange provides a tortuous flowpath to airborne fluid particle migration toward vacuum port 20. Such airborne particles must travel from within container 12 either over rim 50 or upwardly through arcuate apertures 102, then over lip 46 through gap 100, then downwardly between flange 116 and upper basket wall section 44, then around the bottom of flange 116, then through the annular gap 118 between disc lip 88 and inner lower edge 120 of the vacuum port shoulder, in order to reach mouth 90. This tortuous path minimizes airborne fluid particle contamination of the hospital vacuum source. Flange 116 further provides additional guidance for the float at lip 80 near the top of its travel stroke to further assure proper valve-closing alignment.

Raised annular shoulder 96 provides increased structural strength in the vaccum port against downward force thereon during tube insertion down around neck 92. This raised shoulder further provides an increased vertical guide span for the float while still maintaining low profile of the basket beneath the cover. The annular sidewall 122 of the raised shoulder is tapered slightly inwardly as it extends upwardly.

The vertical guiding structure of the present invention, in addition to performing a vertical reciprocatory guiding function, additionally performs a gasket-less sealing function for float 68. This is important for maintaining buoyancy of the float. Reception sleeve 70 integrally extends upwardly from the float bottom 72 and has an integral closed top 74. This guiding structure thus prevents fluid entry into float 68, whereby to maintain buoyancy thereof.

It is recognized that various modifications are possible within the scope of the appended claims.

I claim:

1. In medical suction apparatus including a fluid container with a cover having a patient port for receiving fluid from the body of a patient and a vacuum port for establishing a vacuum in the container for drawing fluid through the patient port, the improvement comprising a basket and float assembly shut-off valve for the vacuum port comprising in combination:
   a basket having a bottom and side walls depending downwardly from said cover below said vacuum port and having one or more upper vacuum communication passages and one or more lower fluid communication openings;
   a float received within said basket and having a peripheral floatation surface;
   said basket and said float having complementally interfitting guiding structure centrally located relative to said peripheral floatation surface for guiding said float upwardly to close said vacuum port in response to rising fluid level in said container entering said basket through said one or more lower openings, said guiding structure including a vertical stalk extending upwardly from the bottom wall of said basket;
   a generally tubular vertical reception sleeve closed at the top and formed integrally with said float for receiving said stalk in telescoping relation; and
   stop means including point contact means between the top of said stalk and the underside of the closed top of said sleeve to provide a gap therebetween to prevent liquid surface-tension impedance to upward movement of said float.

2. The invention according to claim 1 wherein said floatation surface is uniformly concentric about said guiding structure to provide substantially flush floatation thereof and to provide in combination with the maximized surface area afforded thereby an enhanced valve-closing force.

3. The invention according to claim 2 wherein said float carries a flexible sealing gasket which is concave toward and of greater diameter than the vacuum port for peripheral sealing thereof and permitting a limited amount of post-travel of said float upwardly beyond initial seal engagement to improve vertical dimensional deviation tolerance whereby to enable a shorter vertical stroke and afford a shallow low profile shut-off valve.

4. In a medical suction apparatus including a fluid container with a cover having a patient port for receiving fluid from the body of a patient and a vacuum port for establishing a vacuum in the container for drawing fluid through the patient port, the improvement comprising a basket and float assembly shut-off valve for the vacuum port comprising in combination:

a basket having a bottom and side walls depending downwardly from said cover below said vacuum port and having one or more upper vacuum communication passages and one or more lower fluid communication openings;

a float-received within said basket and having a peripheral floatation surface and a bottom;

said basket and said float having complementally interfitting guiding structure centrally located relative to said peripheral floatation surface for guiding said float upwardly to close said vacuum port in response to rising fluid level in said container entering said basket through said one or more lower openings, said guiding structure including a pair of generally tubular vertical sleeves closed at the top thereof, one formed integrally with and extending upwardly from the bottom of said float, the other having a smaller diameter and formed integrally with and extending upwardly from the bottom of said basket, said sleeves slidingly interfitting in reciprocal telescoping relation to provide said guiding structure, and point contact means between the tops of said sleeves providing a gap therebetween and also providing a gap between the bottoms of the float and basket, said gaps preventing liquid surface-tension impedance to upward movement of said float.

5. In medical suction apparatus including a fluid container with a cover having a patient port for receiving fluid and a vacuum port for establishing a vacuum in the container for drawing fluid through the patient port, the improvement comprising a shut-off valve for the vacuum port comprising:

a basket having a bottom and side walls depending downwardly from said cover and having a centrally raised stalk extending upwardly from the bottom thereof; and a float having a centrally raised cavity opening downwardly and receiving said stalk in guiding relation for vertical reciprocal movement thereon, said basket and said float being shallow members generally complementally configured for telescoping reception of said float within said basket in a downward open-valve position of said float;

said basket having one or more lower openings admitting fluid into said basket as the fluid level in the container rises, said basket also having one or more upper passages for vacuum communication between the interior of said container and said vacuum port, such that said float rises along said stalk in response to increasing fluid levels in said basket, and upon reaching a predetermined level, said float closes said vacuum port;

said float having a central upstanding crown with a peripheral rim extending laterally from the base thereof and turned upwardly;

said central crown providing the guiding support for said vertical reciprocal movement of said float along said stalk;

said peripheral rim providing for buoyancy for upward movement of said float in response to increasing fluid levels in said basket;

such that said float is guided centrally to the floatation portion thereof, whereby to afford maximization of floatation surface area to enhance valve closing force of said float; and said floatation surface afforded by said rim is uniformly concentric about said central crown whereby to further afford, in combination with said maximized floatation surface area, flush valve closing with a minimum of vertical guiding structure for said float, whereby to provide a shut-off valve.

6. In medical suction apparatus including a fluid container with a cover having a patient port for receiving fluid and a vacuum port for establishing a vacuum in the container for drawing fluid through the patient port, the improvement comprising a shut-off valve for the vacuum port comprising:

a basket having a bottom and side walls depending downwardly from said cover and having a centrally raised stalk extending upwardly from the bottom thereof;

a float having a centrally raised cavity opening downwardly and receiving said stalk in guiding relation for vertical reciprocal movement thereon;

said basket having one or more openings in the bottom wall to admit fluid into said basket as the fluid level in the container rises, said basket also having one or more upper passages for vacuum communication between the interior of said container and said vacuum port, such that said float rises along said stalk in response to increasing fluid levels in said basket, and upon reaching a predetermined level, said float closes said vacuum port;

the lateral dimension of said basket stalk substantially fills said opening centrally raised float cavity to provide guiding means therefor; and stop means including point contact means between the top of said stalk and the underside of the top wall of said float cavity to provide a gap therebetween to prevent liquid surface-tension impedance to upward movement of said float.

7. The invention according to claim 6 wherein said cup-like basket also has a centrally raised downwardly opening cavity, the exterior side and top of which form said stalk, the vertical dimension of which substantially fills said float cavity in the lowermost position of said float to enable a shallow low-profile shut-off valve.

8. The invention according to claim 7 wherein the outer wall of said basket has an upper peripheral rim extending above the top wall of said basket cavity, and wherein the outer wall of said float has an upper peripheral rim whose upper reach is below the top wall of said float cavity.

9. The invention according to claim 8 wherein the top side of the top wall of said float cavity carries a flexible sealing gasket which is concave toward and of greater diameter than the vacuum port for peripheral sealing thereof and permitting a limited amount of post-travel of said float upwardly beyond initial seal engagement.

10. The invention according to claim 8 wherein said upper peripheral rim of said basket is multi-apertured.

11. Medical suction apparatus for receiving fluid from the body of a patient comprising:

a container;

a cover closing said container and having a patient port for receiving fluid from the body of a patient and a vacuum port for establishing a vacuum in the container for drawing fluid through the patient port;

a basket having a bottom a and side walls attached to the underside of said cover peripherally about said vacuum port and extending therebelow, said basket having an upper annular inwardly spaced rim and a plurality of mounting tabs to receiving slots disposed or said cover supporting said basket such that at least a portion of said rim is spaced a small distance below the underside of said cover to thus provide said one or more vacuum communication passages, said basket further having one or more lower fluid communication openings; and a float disposed within said basket and complementally configured thereto for being centrally guided thereby upwardly to close said vacuum port in response to rising fluid in said container entering said one or more fluid communication openings in said basket to buoy said float along a floatation surface concentric to the central guide provided by said basket.

12. The invention according to claim 11 wherein said basket rim has a flange extending laterally outwardly therefrom with a plurality of arcuate apertures formed therethrough.

13. The invention according to claim 11 wherein said cover has an annular flange extending downwardly from the underside thereof concentric to said vacuum port and centrally located relative to said basket rim and having a lower reach below the upper reach of said basket rim.

14. The invention according to claim 11 wherein said cover has an annular flange extending downwardly from the underside of said cover providing additional guidance for said float near the top of its travel stroke.

15. The invention according to claim 14 wherein said cover flange provides said guidance at the outer periphery of said float.

16. The invention according to claim 11 wherein said vacuum port has a mouth displaced above the main plane of said cover by a raised annular shoulder having a diameter larger than the diameter of said vacuum port to increase structural strength against downward force on said vacuum port and to increase the vertical guide span for said float while still maintaining low profile of said basket beneath said cover.

17. The invention according to claim 11 wherein:

said float has a generally tubular vertical sleeve extending upwardly from the bottom thereof around which is disposed said floatation surface;

said sleeve has a top wall carrying a flexible sealing disc;

said vacuum port has a lower surface defining a mouth; and said disc is concave toward and of greater diameter than said mouth for peripheral sealing thereof upon engagement of said disc with said lower surface in response to upward movement of said float.

18. The invention according to claim 17 wherein:

said disc is centrally disposed on said top wall of said sleeve to provide a lateral span to the periphery of said disc enabling flexure thereof; and said sleeve has an annular auxiliary sealing support extending above said top wall and engaging the undersurface of said disc to provide an additional seal in response to upward movement of said float.

19. The invention according to claim 18 wherein:

said annular auxiliary sealing support is incentric to the outer periphery of said disc; and upward movement of said float effects initial engagement of said disc outer periphery with said lower surface of said vacuum port followed by increasing engagement force of said annular auxiliary sealing support against said undersurface of said disc to provide a seal therebetween and to enhance the seal between said outer periphery of said disc and said lower surface of said vacuum port.

20. The invention according to claim 19 wherein said annular auxiliary sealing support is concentric to said mouth and pinches said disc against said lower surface of said vacuum port in response to further upward movement of said float to afford a back-up seal with annularly localized sealing pressure.

21. Medical suction apparatus for receiving fluid from the body of a patient comprising:

a container;

a cover closing said container and having a patient port for receiving fluid from the body of a patient and a vacuum port for establishing a vacuum in the container for drawing fluid through the patient port; and side walls a basket having a bottom attached to the underside of said cover peripherally about said vacuum port and extending therebelow, said basket having one or more upper vacuum communication passages and one or more lower fluid communication openings;

a float disposed within said basket and complementally configured thereto for being centrally guided thereby upwardly to close said vacuum port in response to rising fluid in said container entering said one or more fluid communication openings in said basket to buoy said float along a floatation surface concentric to the central guide provided by said basket;

said float having a generally tubular vertical sleeve integrally extending upwardly from the bottom thereof around which is disposed said floatation surface; and said basket having a generally tubular vertical sleeve integrally extending upwardly from the bottom thereof and of smaller diameter than said float sleeve;

said sleeves slidingly interfitting in reciprocal telescoping relation to provide said central guiding means.

* * * * *

UNITED STATES PATENT AND TRADEMARK OFFICE
CERTIFICATE OF CORRECTION

PATENT NO. : 4,321,923
DATED : March 30, 1982
INVENTOR(S) : ROBERT L. NICHOLS

It is certified that error appears in the above—identified patent and that said Letters Patent is hereby corrected as shown below:

Col. 5, line 58, "vaccum" should be --vacuum--.

Col. 9, line 8, after "tabs", insert --means for attachment--;
       line 9, "or" should be --on--.

Col. 10, line 35, after "port;", delete --and side walls--;
       line 36, after "bottom", insert --and side walls--.

Signed and Sealed this

First Day of February 1983

[SEAL]

Attest:

GERALD J. MOSSINGHOFF

Attesting Officer    Commissioner of Patents and Trademarks